(12) United States Patent
Sugiura (10) Patent No.: US 6,581,597 B2
(45) Date of Patent: Jun. 24, 2003

(54) HIGH-FREQUENCY OSCILLATION ARTIFICIAL RESPIRATION APPARATUS

(75) Inventor: Yasuhito Sugiura, Shizuoka (JP)

(73) Assignee: Suzuki Motor Corporation, Shizuoka (JP)

( * ) Notice: Subject to any disclaimer, the term of this patent is extended or adjusted under 35 U.S.C. 154(b) by 221 days.

(21) Appl. No.: 09/750,052

(22) Filed: Dec. 29, 2000

(65) Prior Publication Data

US 2001/0007256 A1 Jul. 12, 2001

(30) Foreign Application Priority Data

Jan. 11, 2000 (JP) ...................................... 2000-002235

(51) Int. Cl.[7] ............................................ A61M 16/00
(52) U.S. Cl. ............................. 128/204.21; 128/204.18
(58) Field of Search ...................... 128/204.18, 204.21, 128/204.23, 205.11, 205.16, 911, 912

(56) References Cited

U.S. PATENT DOCUMENTS

| | | | | |
|---|---|---|---|---|
| 4,463,756 A | * | 8/1984 | Thuc ...................... | 128/204.21 |
| 4,747,403 A | * | 5/1988 | Gluck et al. ........... | 128/204.21 |
| 4,788,974 A | * | 12/1988 | Phuc ...................... | 128/204.21 |
| 4,805,612 A | * | 2/1989 | Jensen ................... | 128/204.21 |
| 5,555,880 A | * | 9/1996 | Winter et al. .......... | 128/204.21 |
| 5,692,497 A | * | 12/1997 | Schnitzer et al. ...... | 128/204.18 |
| 5,899,203 A | * | 5/1999 | Defares et al. ........ | 128/204.21 |
| 6,209,540 B1 | * | 4/2001 | Sugiura et al. ........ | 128/204.18 |
| 6,257,234 B1 | * | 7/2001 | Sun ........................ | 128/204.18 |
| 6,415,791 B1 | * | 7/2002 | Van Brunt ............. | 128/200.24 |
| 6,435,182 B1 | * | 8/2002 | Lutchen et al. ........ | 128/200.24 |
| 6,446,629 B1 | * | 9/2002 | Takaki et al. .......... | 128/204.18 |

* cited by examiner

Primary Examiner—Weilun Lo
Assistant Examiner—Mital Patel
(74) Attorney, Agent, or Firm—Greenblulm & Bernstein, P.L.C.

(57) ABSTRACT

The present invention provides a high-frequency oscillation (HFO) artificial respiration apparatus comprising an inhale gas introduction block 62 for supplying an inhale gas to a patient X, a patient-side path 60 for guiding the inhale gas to the patient X, an oscillating air pressure urging block 50 for applying an oscillating air pressure to the inhale gas, an exhaust path 70 for exhausting an exhale gas exhaled from the patient X, and a controller 40 for controlling operation of the oscillating air pressure urging block 50. The oscillating air pressure urging block 50 includes a blower 52 and a rotary valve 54. The controller 40 includes an input block 41 for accepting a ventilation frequency and a ventilation amount at a time for the patient and an operation control block 49 for controlling the rotary valve 54 and the blower 52 according to values entered. The operation control block 49 has a ventilation amount maintaining function 46 for controlling an amplitude defined by the blower 52 so that the ventilation amount at a time for the patient is maintained at a constant value when the oscillation frequency is modified.

12 Claims, 10 Drawing Sheets

| INHALE GAS AMOUNT [ℓ/min] | 10 | 15 | 20 | 25 | 30 |
|---|---|---|---|---|---|
| $M_i$ | $M_1$ | $M_2$ | $M_3$ | $M_4$ | $M_5$ |

FIG.5

| INNER PRESSURE [cmH₂O (Pa)] | 5 (490) | 6 (588) | 7 (686) | 8 (784) | 9 (882) | 10 (980) | 11 (1078) | 12 (1176) | 13 (1274) | 14 (1372) | 15 (1470) |
|---|---|---|---|---|---|---|---|---|---|---|---|
| $M_{ij}$ | $M_{51}$ | $M_{52}$ | $M_{53}$ | $M_{54}$ | $M_{55}$ | $M_{56}$ | $M_{57}$ | $M_{58}$ | $M_{59}$ | $M_{5\alpha}$ | $M_{5\beta}$ |

FIG.6

| FREQUENCY [Hz] | 3 | 6 | 9 | 12 | 15 |
|---|---|---|---|---|---|
| $M_{ijk}$ | $M_{561}$ | $M_{562}$ | $M_{563}$ | $M_{564}$ | $M_{565}$ |

HIGH-FREQUENCY OSCILLATION ARTIFICIAL RESPIRATION APPARATUS

BACKGROUND OF THE INVENTION

1. Field of the Invention

The present invention relates to an artificial respiration apparatus and in particular, to a high-frequency oscillation (HFO) artificial respiration apparatus.

2. Description of Related Art

Figure 11:
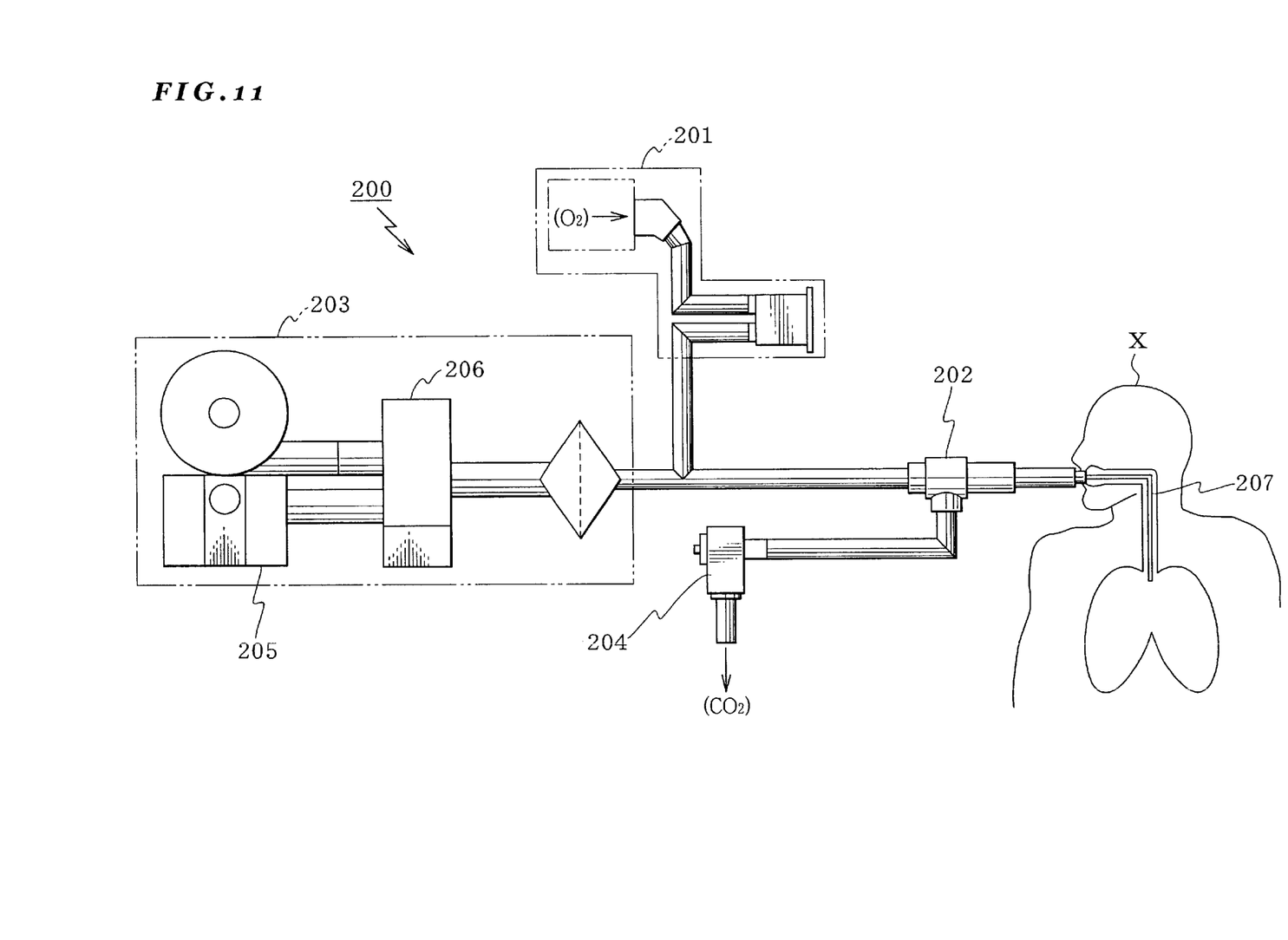
FIG. 11 is a block diagram showing a configuration of a conventional HFO artificial respiration apparatus.

FIG. 11 shows a conventional HFO artificial respiration apparatus 200. An inhale gas containing a high concentration of oxygen flows from an oxygen supply port 201 via a three-way branching pipe 202 to a patient X and to an exhaust end. The inhale gas flows normally at flow rate from 10 to 30 [l/min] and 60 [l/min] at maximum, to which a high frequency oscillating air pressure is applied by an oscillating air pressure urging block 203 for oxygen supply into lungs of the patient X. Here, the average pressure applied to the lungs of the patient X is controlled by an open degree of a rubber valve of an exhale valve 204 provided at an exhaust opening of exhale gas. The oscillating air pressure has an oscillation frequency (hereinafter, referred to as ventilation frequency) adjusted by rpm of a rotary valve 206 of the oscillating air pressure urging block 203 and an amplitude adjusted by an output of a blower 205.

Here, explanation will be given on the principle of the oxygen supply in this HFO artificial respiration apparatus 200. Firstly, when the inhale gas supplied to a patient X is subjected to a HFO air pressure, the pressure amplitude of the inhale gas causes a small-amount ventilation (gas exchange like convection) with respect to the gas (hereinafter, referred to as an exhale gas) containing carbon dioxide in the lungs of the patient X and the dispersion of the inhale gas due to oscillation causes the inhale gas to enter the lungs via an in-trachea tube 207, which in turn causes the exhale gas to go out of the lungs (up to the mouth of the patient). The subsequent inhale gas performs the aforementioned ventilation and functions to send the exhale gas from the lungs to the exhale gas exhaust opening. Thus, it is possible to maintain a constant oxygen concentration in the lungs of the patient X.

The aforementioned HFO artificial respiration apparatus 200 has three basic parameters which can be set by a user (doctor) according to the state of a patient: (1) inner pressure of a patient circuit from the oxygen supply port to the patient X (5 to 15 [$cmH_2O$] (490 to 1470 [Pa]), (2) oscillation amplitude of the high frequency oscillating air pressure (output of the blower 205), and (3) ventilation frequency of the oscillating air pressure (3 to 15 [Hz]). There are also additional parameters: the inhale gas amount supplied to a patient X and the oxygen concentration of the inhale gas. The basic parameters are controlled according to the state of the patient X so as to obtain an optimal respiration condition.

(1) When it is necessary to increase the oxygen partial pressure ($PaO_2$) in the artery blood of the patient X, the average inner pressure of the patient circuit is increased.

(2) In order to reduce the carbon dioxide partial pressure ($PaCO_2$) in the artery blood, the amplitude of the high frequency oscillating air pressure is increased.

(3) The inherent ventilation frequency increasing the ventilation efficiency of the HFO artificial respiration differs depending on each of the patients X as well as on the state of a patient X. Accordingly, the ventilation frequency is controlled so as to be in the vicinity of such an inherent ventilation frequency.

The ventilation frequency is initially determined by the weight of the patient X and adjusted so as to obtain resonance with the body of the patient X to increase the gas (oxygen) diffusion effect, which in turn enables to obtain an effective gas exchange (between the oxygen and the carbon oxide). In general, the ventilation frequency is set to about 15 [Hz] for new-born babies, and to 3 to 10 [Hz] for children and grown-ups.

This ventilation frequency is usually fixed to a constant value unless a sudden change of the state of the patient X is observed. Accordingly, the respiration condition is normally adjusted by the parameters (1) and (2) alone.

On the other hand, when the $PaO_2$ is excessively reduced or the $PaCO_2$ is excessively increased due to a change of the state of the patient X, this means that a change has occurred in the ventilation frequency inherent to the patient X and it is not sufficient to adjust the parameters (1) and (2). That is, the ventilation frequency should be adjusted.

Figure 12:
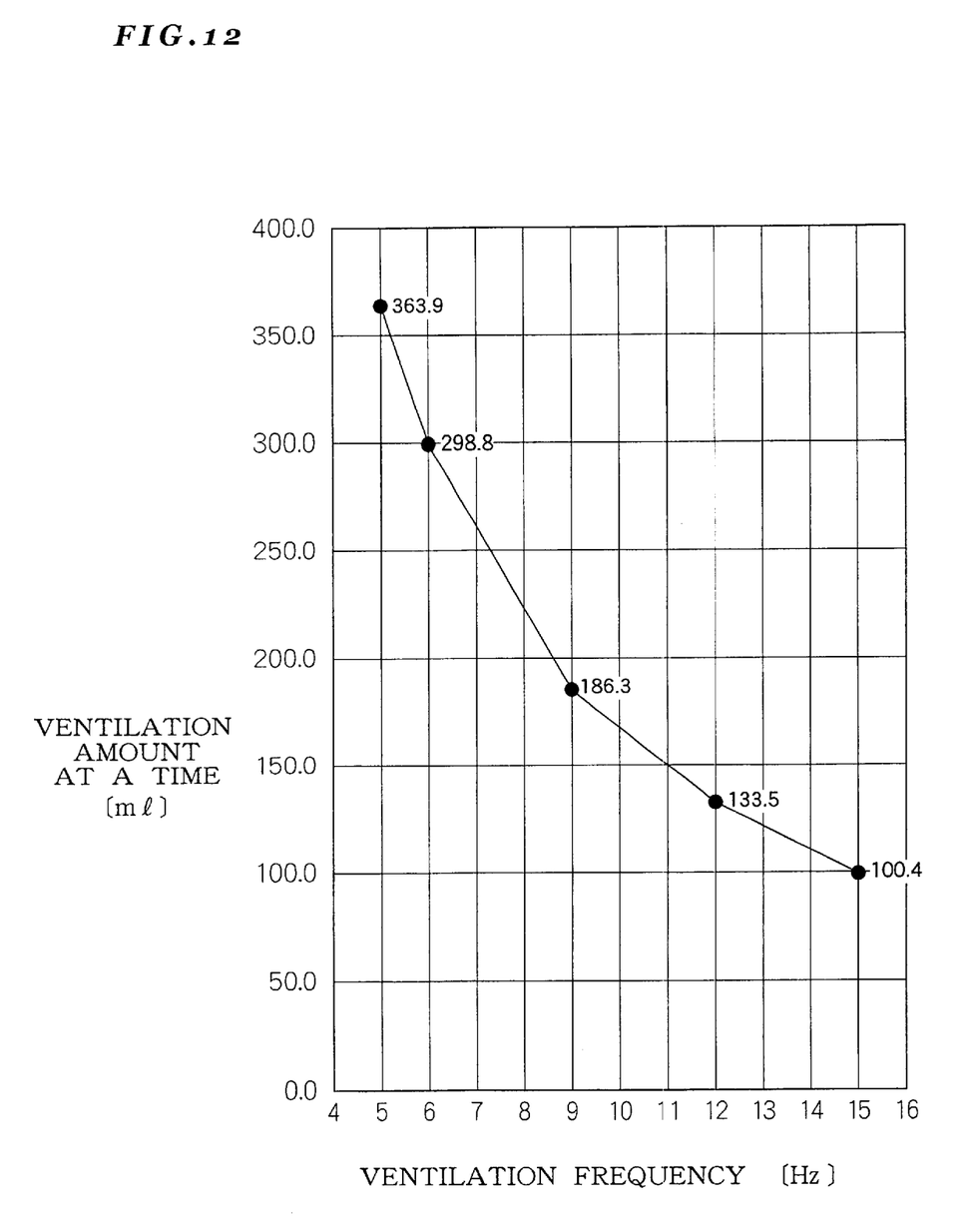
FIG. 12 shows the relationship between the ventilation frequency and the ventilation amount at a time for the lungs of a patient when the blower output is fixed at a drive upper limit in the conventional HFO artificial respiration apparatus.

Here, FIG. 12 shows the relationship between the ventilation frequency and the ventilation amount at a time for the lungs of the patient X when the output of the blower 205 of the oscillating air pressure urging block 203 is fixed to a drive upper limit in the HFO artificial respiration apparatus 200. As shown in FIG. 2, in the HFO artificial respiration apparatus 200, as the ventilation frequency is changed, the ventilation amount at a time is also changed. This is because a change of the ventilation frequency causes a change of the degree of the gas turbulence. For example, when the ventilation frequency is reduced, the flow resistance in the patient circuit is also reduced, and when the ventilation frequency is increased, the flow resistance is also increased.

Accordingly, in the aforementioned conventional example, if the ventilation frequency is reduced while maintaining the blower output constant, the ventilation amount at a time is abruptly increased. Even when the ventilation frequency is reduced only by 1 [Hz], the ventilation amount at a time may be excessively increased.

In order to evade this, the operator (doctor) of the HFO artificial respiration apparatus 200 should slightly reduce the output of the blower 205 by visual observation before changing the ventilation frequency. Moreover, the operator cannot know accurately how much the output of the blower 205 need be reduced. That is, it is difficult to maintain the ventilation amount at a time at a constant value when changing the ventilation frequency.

SUMMARY OP THE INVENTION

It is therefore an object of the present invention to provide a HFO artificial respiration apparatus capable of suppressing the change of the ventilation amount at a time when changing the ventilation frequency without requiring a complicated operation.

The high-frequency oscillation (HFO) artificial respiration apparatus according to the present invention comprises: an inhale gas introduction block for supplying an inhale gas containing oxygen to a patient; a patient-side path for guiding the inhale gas from the inhale gas introduction block to the patient, an oscillating air pressure urging block for applying an oscillating air pressure having a shorter cycle than a respiration cycle of the patient, to the inhale gas flowing in the patient-side path, an exhaust path for exhausting an exhale gas containing carbon dioxide exhaled from the patient; and a controller for controlling the oscillating air pressure urging block. The oscillating air pressure urging block includes an oscillation amplitude regulator for regulating an amplitude of the oscillating air pressure and a frequency regulator for regulating an oscillation frequency of the oscillating air pressure.

The controller includes an input block for accepting setting inputs for specifying an oscillation frequency of the oscillating air pressure and a ventilation amount at a time for the lungs of the patient and an operation control block for controlling the frequency regulator and the amplitude regulator according to the inputs. The operation control block has a ventilation amount maintaining function for controlling an amplitude based on the amplitude regulator in such a manner that the ventilation amount at a time for the lungs of the patient is maintained at a constant value when the oscillation frequency of the frequency regulator is changed by the setting inputs.

With this configuration, an operation of the apparatus enters an oscillation frequency of the oscillating air pressure and the ventilation amount at a time for the lungs of the patient through an external input unit connected to the input block.

The inhale gas introduced from the inhale gas introduction block is sent through the patient-side path up to the patient. The oscillating air pressure provided by the oscillating air pressure urging block is applied to the inhale gas flowing through the patient-side path. The oscillating air pressure is set to the oscillating frequency entered and the amplitude corresponding to the ventilation amount at a time for the lungs of the patient entered.

The inhale gas flows via a branching pipe into the patient-side path and to the exhaust path. The inhale gas flowing to the patient side is driven by a positive pressure of the oscillating air pressure to flow through an in-trachea insert tube into lungs of the patient to supply oxygen into the lungs. On the other hand, an exhale gas containing carbon oxide exhaled from the lungs is driven by a negative pressure of the oscillating air pressure to flow through the in-trachea insert tube into the branching pipe and is pushed into the exhaust path together with a subsequent inhale gas to be exhausted into the atmosphere.

When the patient ventilation efficiency is found to be low and the oscillation frequency is not set properly, or when the state of the patient is suddenly changed, the operator enters a new oscillation frequency value to the input block.

When the oscillation frequency is updated, the operation control block starts an operation control for modifying the oscillation frequency of the oscillating air pressure output from the oscillating air pressure urging block. Here, the operation control is performed not only for the frequency regulator but also for the amplitude regulator.

That is, according to the ventilation amount maintaining function, the operation control block performs an operation control of the amplitude regulator, so as to obtain an amplitude which does not change the ventilation amount at a time for the lungs of the patient.

According to another aspect of the present invention, the controller includes a map memory containing a map using the ventilation amount at a time for the lungs of the patient and the oscillation frequency of the oscillating air pressure as parameters for identifying an appropriate output of the amplitude regulator.

The ventilation amount at a time for the lungs of the patient and the oscillation frequency entered are used to identify a particular amplitude regulator output in the map. Moreover, when the oscillation frequency is modified, a "target value of the oscillation frequency" and a current value of "the ventilation amount at a time for the lungs of the patient" are used to identify a particular amplitude regulator output not changing the current value of the ventilation amount and an operation control is performed to set the output.

According to yet another aspect of the present invention, the map is based on test data obtained by measuring the ventilation amount at a time for the lungs of the patient while changing the output of the oscillating air pressure urging block and the oscillation frequency of the oscillating air pressure.

That is, this map is created from test data obtained by measuring the ventilation amount at a time output form the patient by the HFO artificial respiration apparatus while changing each of the output of the oscillating air pressure urging block and the oscillation frequency of the oscillating air pressure within a practical range. This test data clarifies the relationship between the output of the oscillating air pressure urging block, the oscillation frequency of the oscillating air pressure, and the ventilation amount at a time. Accordingly, when a ventilation amount and an oscillation frequency are specified, it is possible to identify a corresponding output of the amplitude regulator. That is, it is possible to know the output of the amplitude regulator to obtain a desired ventilation amount at a time and the operator can set the ventilation amount at a time for the lungs of the patient at an appropriate value.

According to still another aspect of the present invention, the apparatus further comprises an input unit connected to the controller for entering the ventilation amount at a time for the lungs of the patient and the oscillation frequency of the oscillating air pressure.

With this configuration, the operator can enter the aforementioned values through the input unit.

According to still yet another aspect of the present invention, the apparatus further comprising a display block connected to the controller for displaying a predetermined information, wherein the operation control block has an output upper limit maintaining function, used when a target output of the oscillation regulator defined by the ventilation amount maintaining function exceeds a drive upper limit, for controlling the target output to be at the drive upper limit as well as displaying a corresponding ventilation amount at a time for the lungs of the patient on the display block.

Here, the term "drive upper limit" is a value set, considering the maintenance of the amplitude regulator and does not represent a physical limit of the amplitude regulator. However, this drive upper limit may also be matched with the physical limit.

When the oscillation frequency is specified to be increased to a value under which the amplitude regulator output exceeds the upper limit in order to maintain the current ventilation amount at a time, an operation control is performed in such a manner that the output of the oscillation regulator is fixed at the upper limit.

Since the amplitude determined by the aforementioned control is not sufficient to maintain the current ventilation amount for the lungs of the patient, the ventilation amount is reduced to a value which is obtained from the oscillation regulator output and the oscillation frequency and displayed on the display block.

DESCRIPTION OF THE PREFERRED EMBODIMENTS

[Entire Configuration]

Figure 1:
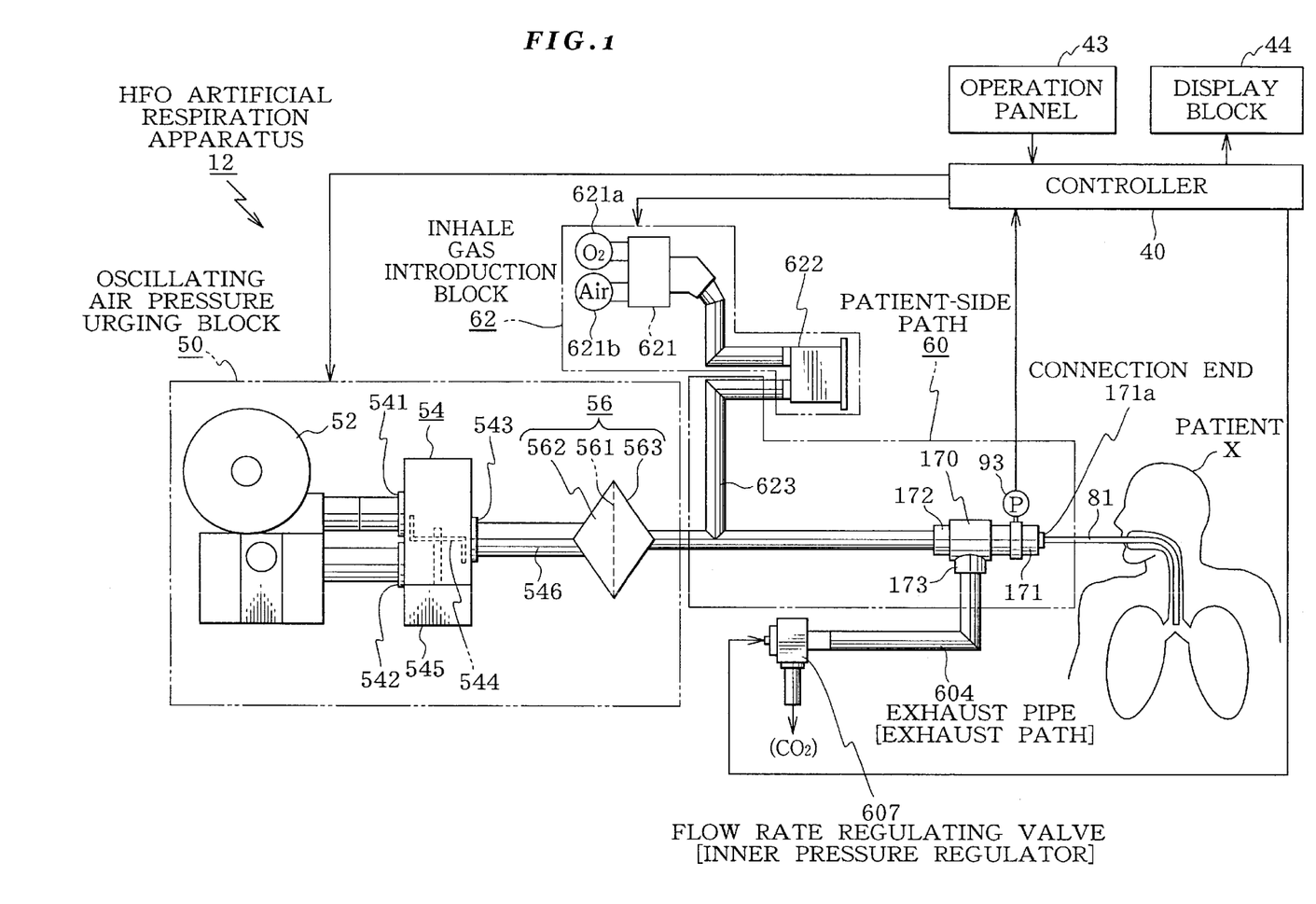
FIG. 1 is a block diagram showing a configuration of a HFO artificial respiration apparatus according to an embodiment of the present invention.

Description will now be directed to an embodiment of the present invention with reference to FIG. 1 to FIG. 10. FIG. 1 is a block diagram showing a configuration of a high frequency oscillation (HFO) artificial respiration apparatus 12 according to the present embodiment.

The HFO artificial respiration apparatus 12 includes: an inhale gas introduction block 62 for supplying an inhale gas containing oxygen to a patient X; a patient side path 60 for guiding the inhale gas from the inhale gas introduction block 62 to the patient X; an oscillating air pressure urging block 50 for applying to the inhale gas flowing through this patient side path 60 an oscillating air pressure having a shorter cycle than the respiration cycle of the patient X; an exhaust path (exhaust pipe 604) for exhausting into the atmosphere an exhale gas containing carbon dioxide exhaled from the patient X; a flow rate regulating valve 607 for regulating the average inner pressure in the patient-side path 60 and the exhaust pipe 604 as an exhaust path; and a controller 40 for controlling operations of respective components of the artificial respiration apparatus 12.

Explanation will be given on the respective components.

[Inhale Gas Introduction Block]

The inhale gas introduction block 62 includes an oxygen supply port 621a, an air supply port 621b, a blender 621 as first regulation means for mixing the oxygen and the air, and a humidifier 622 for humidifying the air sent out from the blender 621.

The oxygen supply port 621a includes a cylinder containing oxygen or an oxygen supply valve arranged in a hospital facility. Similarly, the air supply port 621b includes a cylinder containing air or an air supply valve arranged in a hospital facility. The supply ports 621a and 621b supply oxygen and air under a predetermined pressure.

The blender 621 includes a flow rate regulating valve (not depicted) at each of the connections to the supply ports 621a and 621b. By adjusting these valves, it is possible to adjust the oxygen concentration of the inhale gas. Moreover, the blender 621 includes an output valve (not depicted) for regulating the supply of the inhale gas to the humidifier 622. It should be noted that the oxygen concentration and the flow rate of the inhale gas are automatically set by operation signals from the controller 40.

The humidifier 622 is connected to an inhale gas pipe 623 for supplying the humidified inhale gas to a patient X. The inhale gas pipe 623 is branched to a pressurized chamber 563 of a diaphragm mechanism 56 and to a three-way branching pipe 170.

[Oscillating Air Pressure Urging Block]

The oscillating air pressure urging block 50 includes: a blower 52 as an amplitude regulator for simultaneously generating positive and negative air pressure; a rotary valve mechanism 54 as a frequency regulator for alternately selecting the positive and the negative pressure generated by the blower 52 and converting them into a predetermined oscillating air pressure; and a diaphragm mechanism 56 urged to operate by the oscillating air pressure from the rotary valve mechanism 54 and applying an oscillating air pressure to the inhale gas supplied from the inhale gas introduction block 62 to the patient X.

The blower 52 takes in air and sends out the air so as to simultaneously generate a positive and negative pressure. The blower 52 has an air intake hole connected to a negative pressure port 542 of the rotary valve mechanism 54 and an air send-out hole connected to a positive pressure port 541.

The blower 52 includes a fan and a motor for rotating the fan. The motor includes an inverter whose output is controlled by the controller 40 so as to adjust the air send-out amount and the oscillating air pressure amplitude Apn.

The rotary valve mechanism 54 includes: the positive pressure port 541 supplied with the positive pressure from the blower 52; the negative pressure port 542 supplied with the negative pressure from the blower 52; an output port 543 for outputting the oscillating air pressure; a rotary valve 544 rotating to alternately connect the output port 543 to the positive pressure port 541 and to the negative pressure port 542; and a drive block 545 for rotating the rotary valve 544.

The drive block 545 includes a motor (not depicted) and a reducer (not depicted) so as to rotate the rotary valve 544 at rpm specified by the controller 40. While the rotary valve 544 makes one turn, the positive pressure port 541 is once connected to the output port 543 and the negative pressure port 542 is once connected to the output port 543. Thus, the oscillating air pressure Apn having an oscillation frequency proportional to the rpm of the drive block 545 is applied to the inhale gas supplied. The controller 40 controls the rpm of the drive block 545 so as to control the oscillating frequency (ventilation frequency) of the oscillating air pressure Apn.

Moreover, as has been described above, the controller 40 also controls the amount of the air sent out from the blower 52. By adjusting the air send-out amount according to the aforementioned oscillating frequency, it is possible to adjust the ventilation amount at a time in the oscillating air pressure urging block 50 (amplitude per oscillation cycle of the oscillating air pressure Apn).

It should be noted that the output port 543 is connected to an oscillating air pressure pipe 546 for transmitting the oscillating air pressure Apn to the diaphragm mechanism 56.

The diaphragm mechanism 56 includes a pressurizing chamber 562, a pressurized chamber 563, and a diaphragm 561 made from an expandable film member to serve as a partition between the pressurizing chamber 562 and the pressurized chamber 563. The pressurizing chamber 562 is connected via the oscillating air pressure pipe 546 to the output port 543 of the rotary valve 54 while the pressurized chamber 563 is connected to the inhale gas pipe 623. With this configuration, the oscillating air pressure generated by the rotary valve 54 is applied via the diaphragm 561 to the inhale gas flowing in the inhale gas pipe 623. This diaphragm mechanism 56 prevents flow of the air from the oscillating air pressure urging block 50 to the patient's side and prevents contamination of the air and the inhale gas.

[Patient Side Path]

Furthermore, the HFO artificial respiration apparatus 12 includes a three-way branching pipe 170 at the downstream of the inhale pipe 623, which is branched to the patient X side and the exhaust path side. The three-way branching pipe 170 has three pipe portions: a patient side pipe portion 171, an oxygen supply pipe portion 172, and an inhale gas exhaust pipe portion 173 which are connected internally to one another. The oxygen supply pipe portion 172 is connected to the inhale gas pipe 623. The patient side pipe portion 171 has a connection end 171a to which an in-trachea insert tube 81 is detachably connected.

The three-way branching pipe 170, the inhale gas pipe 623, and the in-trachea insert tube 81 constitute a patient-side path 60. Moreover, the patient-side pipe portions 171 is provided with a patient-side pressure sensor 93 and a pressure detected is output to the controller 40.

The in-trachea insert tube 81 has a mounting end connected to the connection end 171a and an insert end inserted through a mouth into the trachea of the patient. The insert end is inserted up to the first branching point where the trachea is branched to the right and left bronchi. Accordingly, the in-trachea insert tube 81 a length sufficient to reach the first branching point and a diameter which can be inserted into the trachea.

For example, in the case of a grown-up male, the length from his mouth to the first branching point is about 22 to 26 [cm] and an additional 3 to 5 [cm] is required as a distance from the patient-side pipe portion 171 of the three-way branching pipe 170 to the patient's mouth. Accordingly, a total length of 25 to 31 [cm] is sufficient for the in-trachea insert tube 81. In this embodiment, the in-trachea insert tube 81 is set to 30 [cm]. As for the diameter of the in-trachea insert tube 81, four variations are available: 3 [mm], 5 [mm], 6 [mm], and 8 [mm] which can be selected according to the inner diameter of the trachea of the patient X. In general, for a grown-up patient, the in-trachea insert tube 81 having the diameter of 8 [mm] is used.

Furthermore, the in-trachea insert tube 81 is detachably connected to the connection end 171a and can easily be replaced. Accordingly, an in-trachea insert tube 81 which has been used for an artificial respiration can be disconnected and discarded or sterilized for reuse.

[Exhaust Path]

The inhale gas exhaust side pipe portion 173 of the three-way branching pipe 170 is connected to one end of an exhaust pipe 604 constituting an exhaust path. The other end of this exhaust pipe 604 is connected to the flow rate regulating valve 607 serving as an inner pressure regulator. The exhaust pipe 604 and the flow rate regulating valve 607 constitutes a path for flow of an exhale gas containing carbon dioxide exhaled from the lungs of the patient X.

Figure 2:
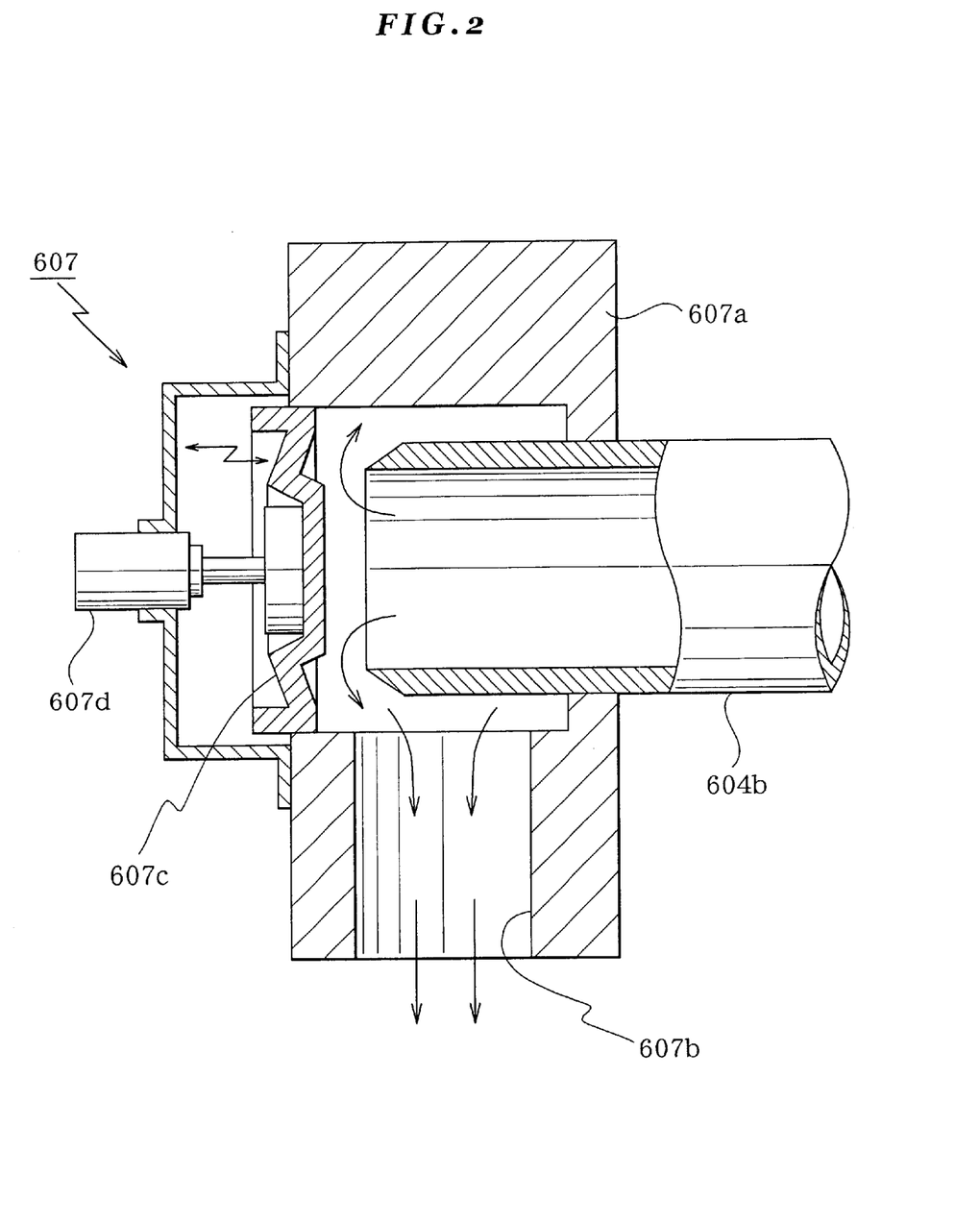
FIG. 2 is a detailed cross sectional view of a flow regulating valve shown in FIG. 1.

FIG. 2 is an enlarged view of the flow rate regulating valve 607 partially cut off. As shown here, the flow rate regulating valve 607 includes a frame 607a, a gas exhaust port 607b, a movable valve (control silicon sheet) 607c for flow rate regulation, and a solenoid 607d as a reciprocal urging mechanism for moving the movable valve 607c forward and backward in a predetermined direction.

The solenoid 607d displaces the movable valve 607c by a displacement amount according to a control signal from the controller 40, thereby adjusting the exhale gas exhaust amount through the flow rate regulating valve 607. Since the patient-side path 60 communicates with the gas exhaust pipe 604, adjustment of the exhale gas exhaust amount also enables to adjust the inner pressure not only in the exhaust pipe 604 but also in the patient-side path 60.

[Controller]

Figure 3:
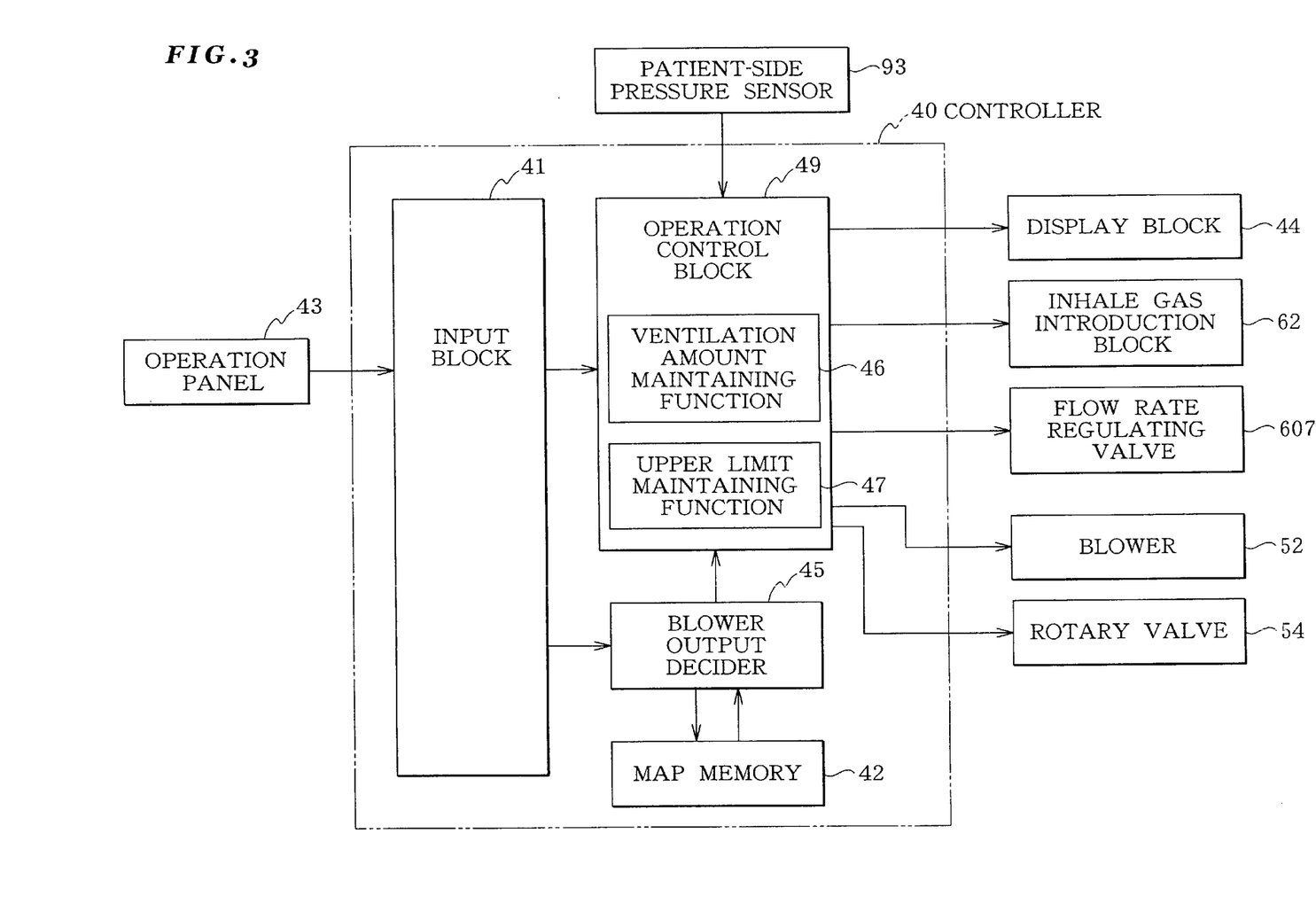
FIG. 3 is a block diagram showing a control system of the HFO artificial respiration apparatus shown in FIG. 1.
Figure 4:
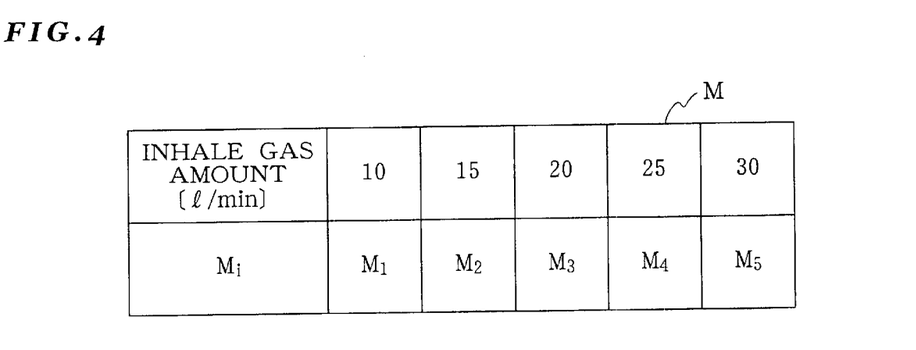
FIG. 4 explains a concept of a first-stage map of a five-dimensional map.

Next, explanation will be given on the controller 40 with reference to FIG. 1 and FIG. 3. FIG. 3 is a block diagram showing a control system of the HFO artificial respiration apparatus 12. The controller 40 includes a CPU, a ROM, and an A/D converter as well as a program for executing the operation control of the HFO artificial respiration apparatus 12.

The controller 40 includes an operation panel 43 to be operated by a doctor (i.e., operator of the HFO artificial respiration apparatus 12) to enter operation conditions for the HFO artificial respiration apparatus 12 and a display block 44 showing the ventilation amount at a time for the lungs of the patient X.

Furthermore, the controller 40 include: an input block 41 for accepting conditions specified from the operation panel 43; an operation control block 49 for controlling the oscillating air pressure urging block 50, the inhale gas introduction block 62, and the flow rate regulation valve 607 according to the values entered to the input block 41; a map memory 42 storing a five-dimensional map which will be detailed later; and a blower output decider 45 for deciding the output of the blower 52 according to the values accepted at the input block 41 using the five-dimensional map and supplying the obtained value to the operation control block 49.

The operation panel 43 is, for example, a keyboard through which the doctor as the operator of the HFO artificial respiration apparatus 12 can enter the ventilation amount at a time for the lungs of the patient X, the oscillation frequency of the oscillating air pressure (hereinafter, referred to as a ventilation frequency), the inhale gas supply amount, the average inner pressure in the patient-side path 60, the diameter of the in-trachea insert tube 81 selected, and the oxygen concentration of the inhale gas.

These operation condition values entered via the operation panel 43 are stored in the input block 41. The input block 41 is a memory for temporary storage. When new operation conditions are entered, they are overwritten over old operation conditions. That is, the operation conditions are updated when new operation conditions are entered.

Moreover, the display block 44 is, for example, a liquid crystal panel. The aforementioned operation conditions entered to the input block 41 are displayed on this display block 44 by control of the operation control block 49.

Next, explanation will be given on the map memory 42. The map memory 42 stores the five-dimensional map for deciding the output of the oscillating air pressure urging block 50 (i.e., output of a drive motor of the blower 52) using five variables: a desired ventilation amount at a time for the lungs of a patient X, a ventilation frequency, an inhale gas supply amount, an average inner pressure in the patient-side path 60, and a diameter of the selected in-trachea insert tube 81.

The five-dimensional map is prepared according to a data obtained from an experiment for measuring the ventilation amount at a time at the insert end of the in-trachea insert tube 81 while changing the output of the oscillating air pressure urging block 50, the ventilation frequency, the inhale gas supply amount, the average inner pressure, and the diameter of the in-trachea insert tube 81.

In other words, this five-dimensional map is based on numerous test data obtained by checking the relationship between the drive motor output of the blower 52 and the ventilation amount at a one cycle of the oscillating air pressure observed at the insert end of the in-trachea insert tube 81 for each of the four different diameters of the in-trachea insert tube 81 while changing each of the inhale gas supply amount, the average inner pressure in the patient-side path 60, and the ventilation frequency in a stepped manner.

Accordingly, when an inhale gas supply amount, an average inner pressure of the patient-side path 60, a ventilation frequency, and a diameter of the in-trachea insert tube 81 are specified, one test data can be specified associated with the relationship between the drive motor output of the blower 52 and the ventilation amount at one cycle of the oscillating air pressure observed at the insert end of the in-trachea insert tube 81.

It should be noted that in this embodiment, a lung model having pressure sensor was arranged at the insert end of the in-trachea insert tube 81 and the ventilation amount per cycle of the oscillating air pressure observed was used as the "ventilation amount at a time for the lungs of the patient". This is because it has been confirmed experimentally that in the HFO artificial respiration, the ventilation amount at a time for the lungs of the patient X is not significantly affected by the lung volume or the compliance and fluctuates according to the inhale gas supply amount, the average inner pressure, the ventilation frequency, the oscillating air pressure amplitude, and the inner diameter of the in-trachea inert tube 81.

In the blower output decider 45, an output of the blower 52 is identified in the aforementioned test data corresponding to the desired ventilation amount at a time. By driving the drive motor of the blower 52 with the identified output, it is possible to perform a HFO artificial respiration with the ventilation amount at a time for the lungs of the patient X desired by the operator.

The five-dimensional map will now be detailed with reference to FIG. 4 to FIG. 7. Firstly, the five-dimensional map includes a first-stage map, shown in FIG. 4, for specifying an inhale gas supply amount which identifies a second-stage map $M_i$. In the first-stage map M, it is possible to specify the inhale gas supply amount in five steps. For example, when 30 [ml] is specified for the inhale gas supply amount, $M_5$ is identified as the second-stage map $M_i$.

Figure 5:
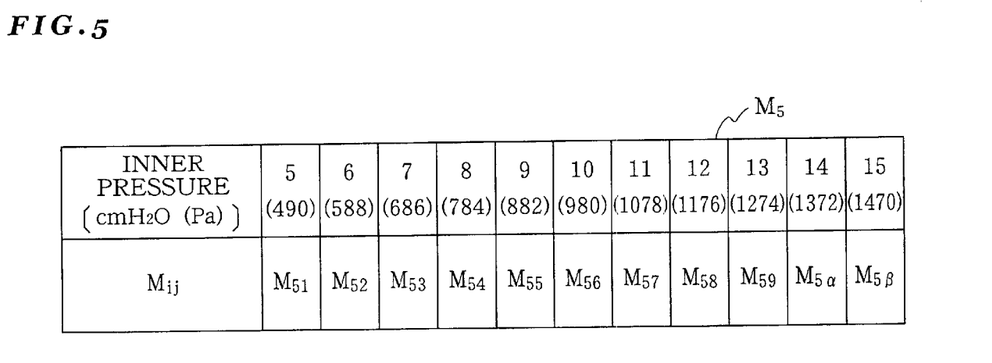
FIG. 5 explains a concept of a second-stage map of the five-dimensional map.

In the second-stage map $M_i$, it is possible to specify the average inner pressure in eleven steps. FIG. 5 shows the $M_5$ map as an example. When 10 [cmH$_2$O] (980 Pa) is specified in the second-stage map $M_5$, for example, $M_{56}$ is identified as the third-stage map $M_{ij}$.

Figure 6:
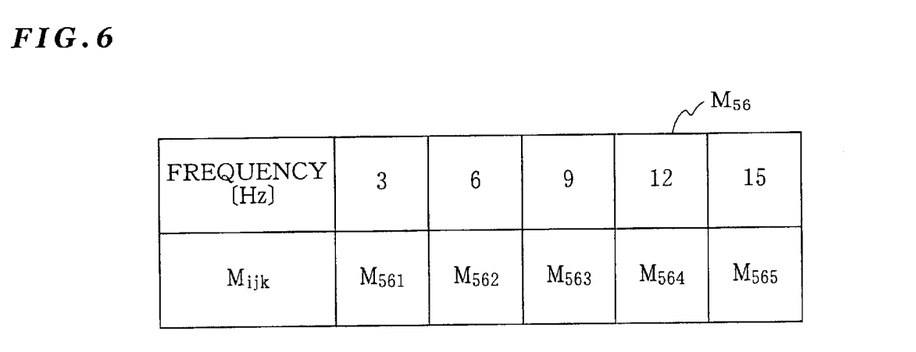
FIG. 6 explains a concept of a third-stage map of the five-dimensional map.

In the third-stage map $M_{ij}$, it is possible to specify the ventilation frequency in five steps. When 15 [Hz] is specified for the ventilation frequency in the third-stage map $M_{56}$, for example, the $M_{565}$ map is identified as the last-stage map $M_{ijk}$.

Figure 7:
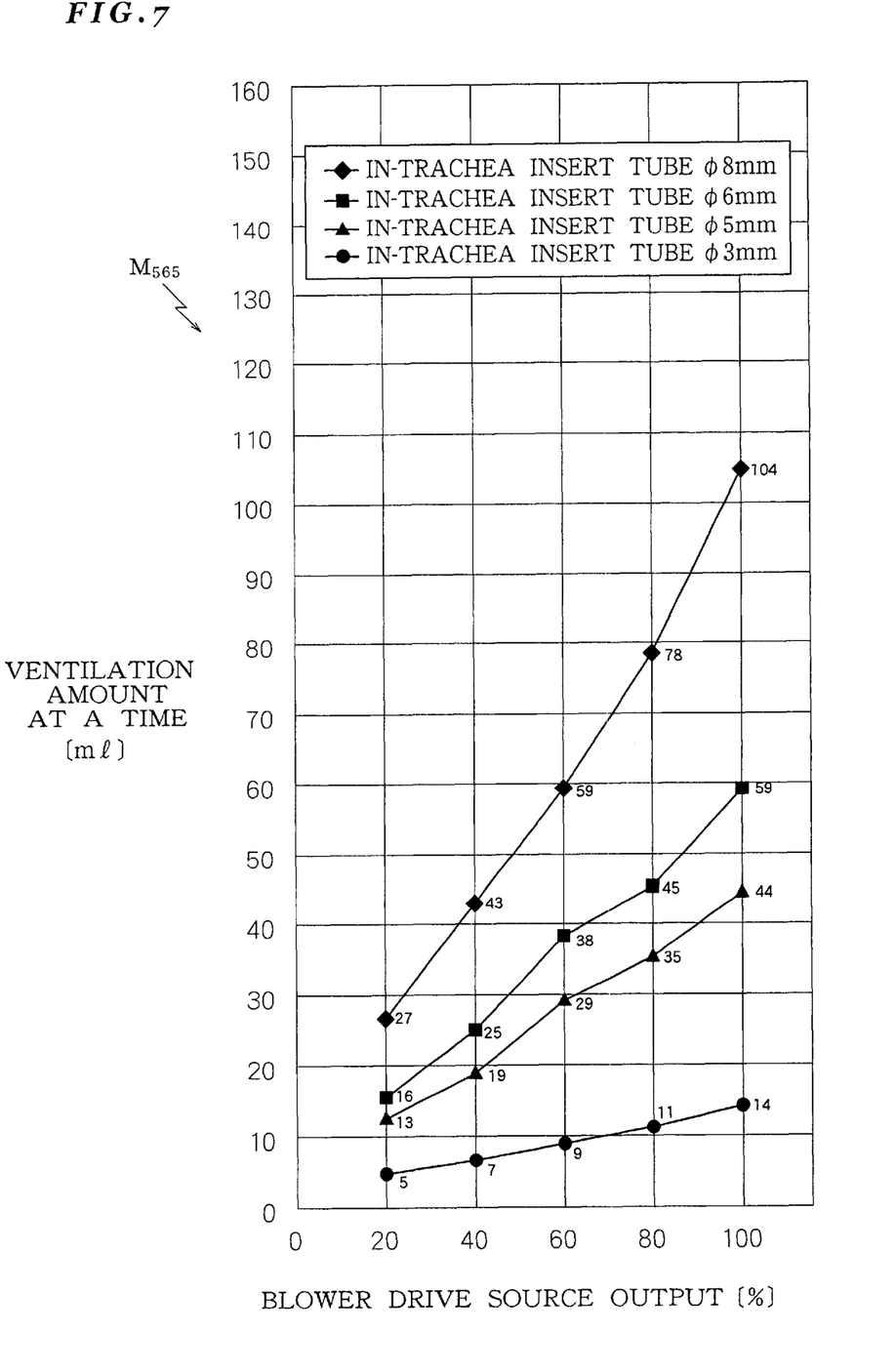
FIG. 7 explains a concept of a last-stage map of the five-dimensional map.

The last-stage map $M_{ijk}$ includes a test data associated with the relationship between the output of the blower 52 and the ventilation amount at a time for the lungs of the patient x obtained by measurements for the four different diameters of the in-trachea insert tube 81 under the specified conditions of the inhale gas supply amount, the average inner pressure, and the ventilation frequency. FIG. 7 graphically shows the last-stage map $M_{565}$ as an example. According to this map, when a HFO artificial respiration is to be performed by using the in-trachea insert tube 81 having the diameter of 8 [mm] and setting 78 [ml] for the ventilation amount at a time for the lungs of the patient X, the output of the drive motor of the blower 52 is automatically set to 80 [%].

Based on the five-dimensional map having the aforementioned configuration, an optimal output of the drive motor of the blower 52 is automatically identified by specifying the inhale gas supply amount, the average inner pressure, the ventilation frequency, the in-trachea insert tube diameter, and the desired ventilation amount at a time. It should be noted the parameters specified in the aforementioned numbers of steps may be adapted so as to be specified in more detailed steps by collecting more test data, thereby enabling to set the ventilation amount at a time for the lungs of the patient X further accurately.

The blower output decider 45 identifies an optimal motor output of the blower 52 in the aforementioned five-dimensional map according to the parameters entered to the input block 41 and outputs the optimal value to the operation control block 49.

The operation control block 49 references the oxygen concentration of the inhale gas stored in the input block 41 and performs an operation control so that the vales of the supply ports 621a and 621b of the blender 621 of the inhale gas introduction block 62 are set to a predetermined open degree. Simultaneously with this, the operation control block 49 references the inhale gas supply amount in the input block 41 and performs an operation control so that the output valve of the blender 621 of the inhale gas introduction block 62 to is set to a predetermined open degree.

Moreover, the operation control block 49 references the average inner pressure stored in the input block 41 and performs an operation control so that the flow rate regulating valve 60 is set to such an open degree that the detected value of the patient-side pressure sensor 93 coincides with the value stored.

Furthermore, the operation control block 49 references the ventilation frequency stored in the input block 41 and performs an operation control to adjust the rpm so that the drive block 545 of the rotary valve 54 of the oscillating air pressure urging block 50 coincides with the ventilation frequency stored. Moreover, the operation control block 49 performs an operation control of the oscillating air pressure urging block 50 according to the blower output specified by the blower output decider 45 referencing the five-dimensional map corresponding to the ventilation amount at a time for the lungs of the patient X stored in the input block 41.

The operation control block 49 includes a ventilation amount maintaining function 46 for controlling the output of the blower 52 in such a manner that the ventilation amount at a time for the lungs of the patient X is maintained at a constant value when changing the ventilation frequency of the rotary valve 54 according to a value specified as well as a drive upper limit maintaining function 47 for maintaining the drive upper limit of the blower 52 if a target value controlled by the ventilation amount maintaining function 46 exceeds the output upper limit and displaying a corresponding ventilation amount at a time for the lungs of the patient X at the display block 44.

Figure 8:
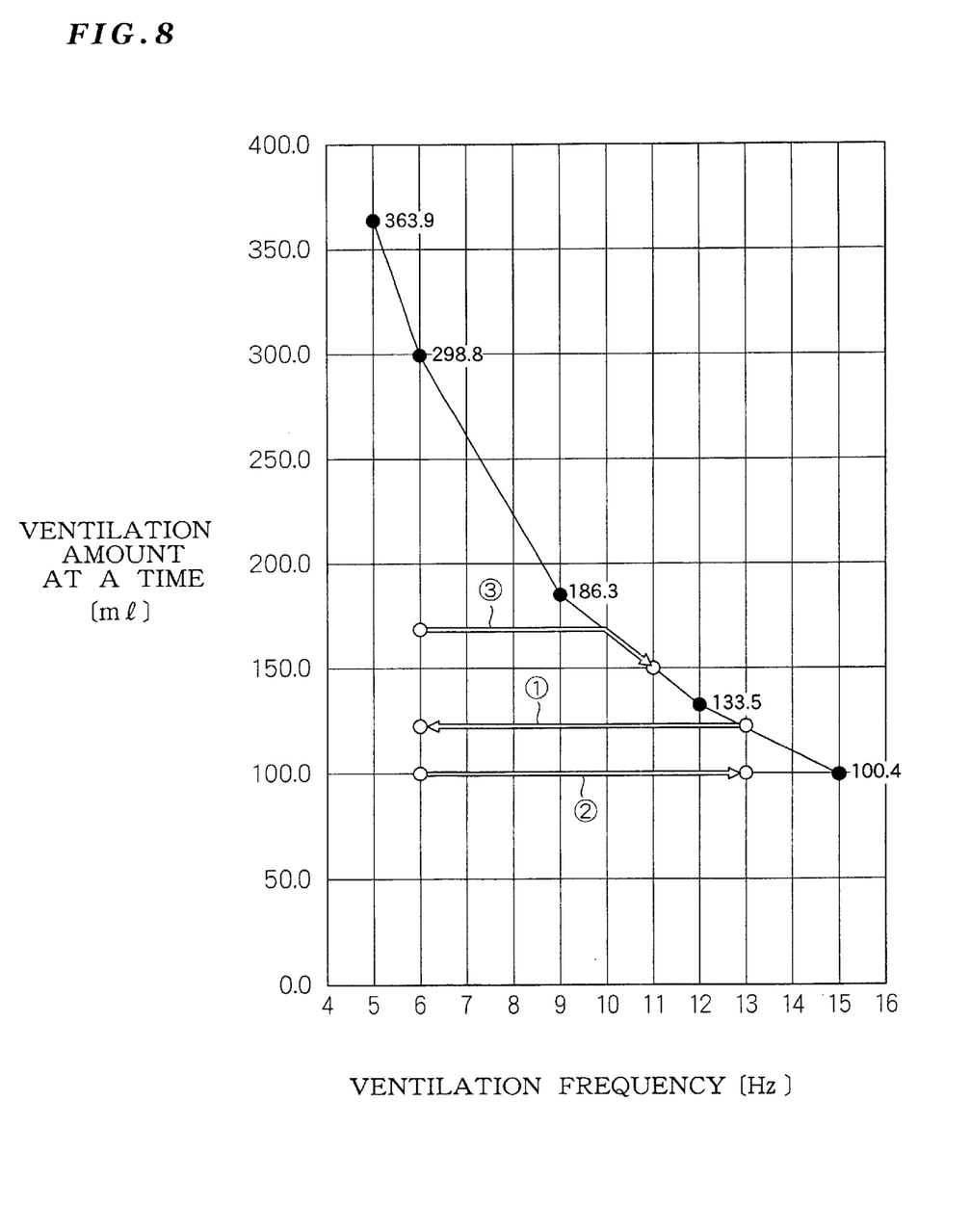
FIG. 8 shows the relationship between the ventilation amount at a time and the ventilation frequency obtained from the pressure in a lung model when the ventilation frequency is changed while the blow output is set to the drive upper limit.

Explanation will now be given on these functions 46 and 47 with reference to FIG. 8. FIG. 8 shows a change of the ventilation amount at a time calculated from a pressure in a lung model (almost identical to the ventilation amount at a time for the lungs of the patient) when the ventilation frequency is changed while maintaining the inhale gas flow rate and the average inner pressure at constant values and the output of the blower 52 at the drive upper limit value and using the in-trachea insert tube 81 having an inner diameter of 8 [mm] in the HFO artificial respiration apparatus 12.

The ventilation amount maintaining function 46 is actuated when a new ventilation frequency value is entered after an inhale gas flow rate, an inhale gas oxygen concentration, an average inner pressure, an inner diameter of the in-trachea insert tube 81, a ventilation frequency, and a ventilation amount at a time for th lungs of the patient have been entered to the input block 41. When a new ventilation frequency value is set, the operation control block 49 performs an operation control for changing the preceding ventilation frequency value to the new ventilation frequency value with respect to the rotary valve 54. Here, if the ventilation frequency is increased while the output of the blower 52 is maintained constant, the oscillating air pressure amplitude is reduced, which in turn reduces the ventilation amount at a time for the lungs of the patient X. On the contrary, if the ventilation frequency is reduced while the output of the blower 52 is maintained constant, the oscillating air pressure amplitude is increased, which in turn increases the ventilation amount at a time for the lungs of the patient X. In order to evade such a change in the ventilation amount at a time, the output of the blower 52 is controlled so as to compensate the change in the ventilation amount at a time.

Accordingly, when performing the operation control of the rotary valve 54 upon modification of the ventilation frequency, the blower 52 is controlled according to a blower output identified in the aforementioned five-dimensional map containing the current inhale gas supply amount, average inner pressure, inner diameter of the in-trachea insert tube 81, the ventilation amount at a time for the lungs of the patient X, and a new ventilation frequency. For example, an arrow (1) in FIG. 8 shows a case when the ventilation frequency is changed from 13 [Hz] to 6 [Hz] while maintaining the ventilation amount at a time for the lungs of the patient at 124 [ml], and an arrow (2) shows a case when the ventilation frequency is changed from 6 [Hz] to 13 [Hz] while maintaining the ventilation amount at a time at 100 [ml]. Thus, the ventilation amount at a time for the lungs of the patient can be maintained at a constant value.

Moreover, the drive upper limit maintaining function 47 is actuated when an excessively high ventilation frequency is set. As has been described above, when the ventilation frequency is increased, the blower output should be increased so as to maintain the ventilation amount at a time. However, an upper limit value of the drive is set for the blower output. If the blower output identified in the blower output decider 45 exceeds the upper limit, the blower output is fixed at the upper limit by the drive upper limit maintaining function 47. An arrow (3) shows a case when the ventilation frequency is changed from 6 [Hz] to 11 [Hz] while maintaining the ventilation amount at a time at 168 [ml]. In this case, when the ventilation frequency exceeds 10 [Hz], it becomes difficult to maintain the ventilation amount at a time for the lungs of the patient X at a constant value and the ventilation amount is decreased as shown in the graph of FIG. 8. Here, it is known that the blower output is currently at 100 [%] as well as the new ventilation frequency, the current inhale gas supply amount, the average inner pressure, and the in-trachea insert tube inner diameter are known values. Accordingly, it is possible to identify a ventilation amount at a time for the lungs of the patient X from the aforementioned five-dimensional map. The operation control block 49 performs an operation control to display the obtained value at the display block 44.

[Operation of the Embodiment]

Figure 9:
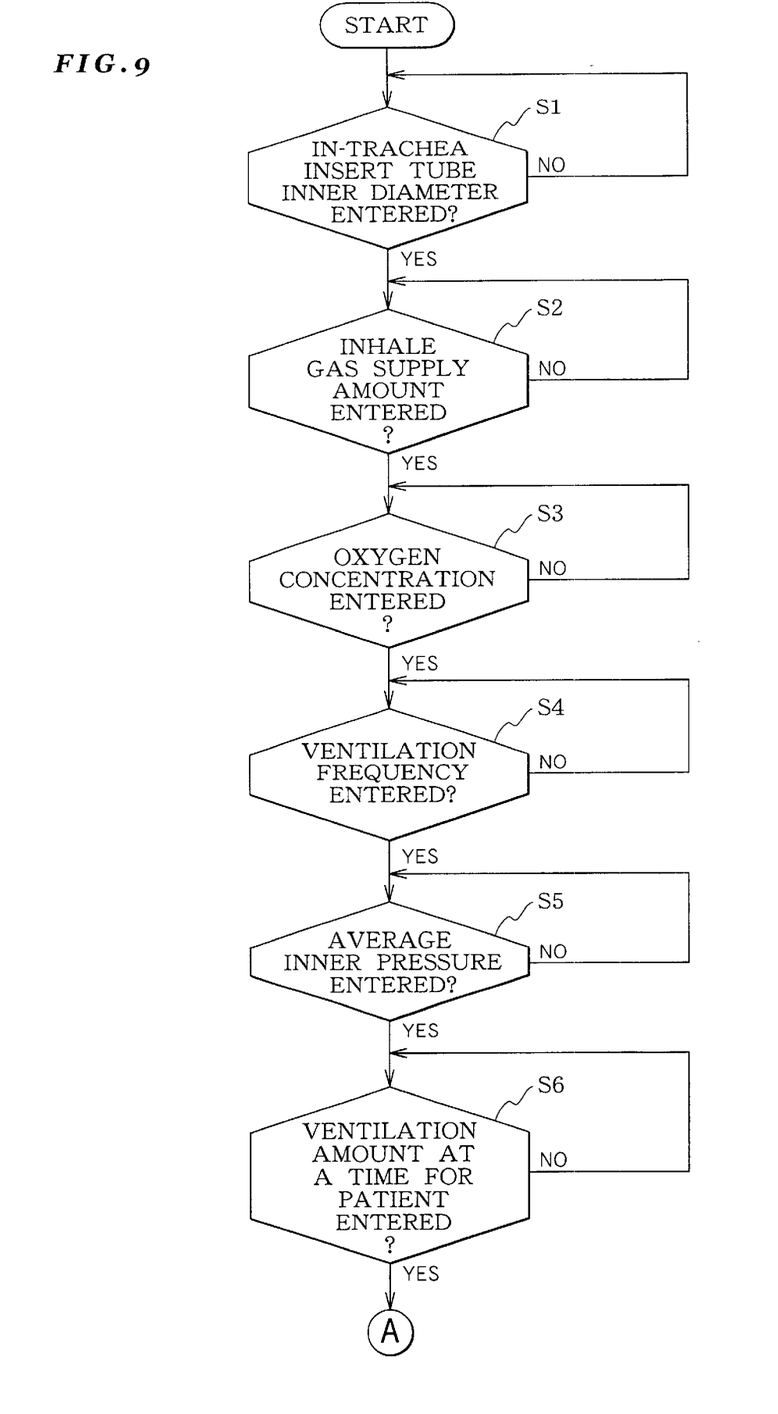
FIG. 9 is a flowchart showing the operation of the HFO artificial respiration apparatus shown in FIG. 1.
Figure 10:
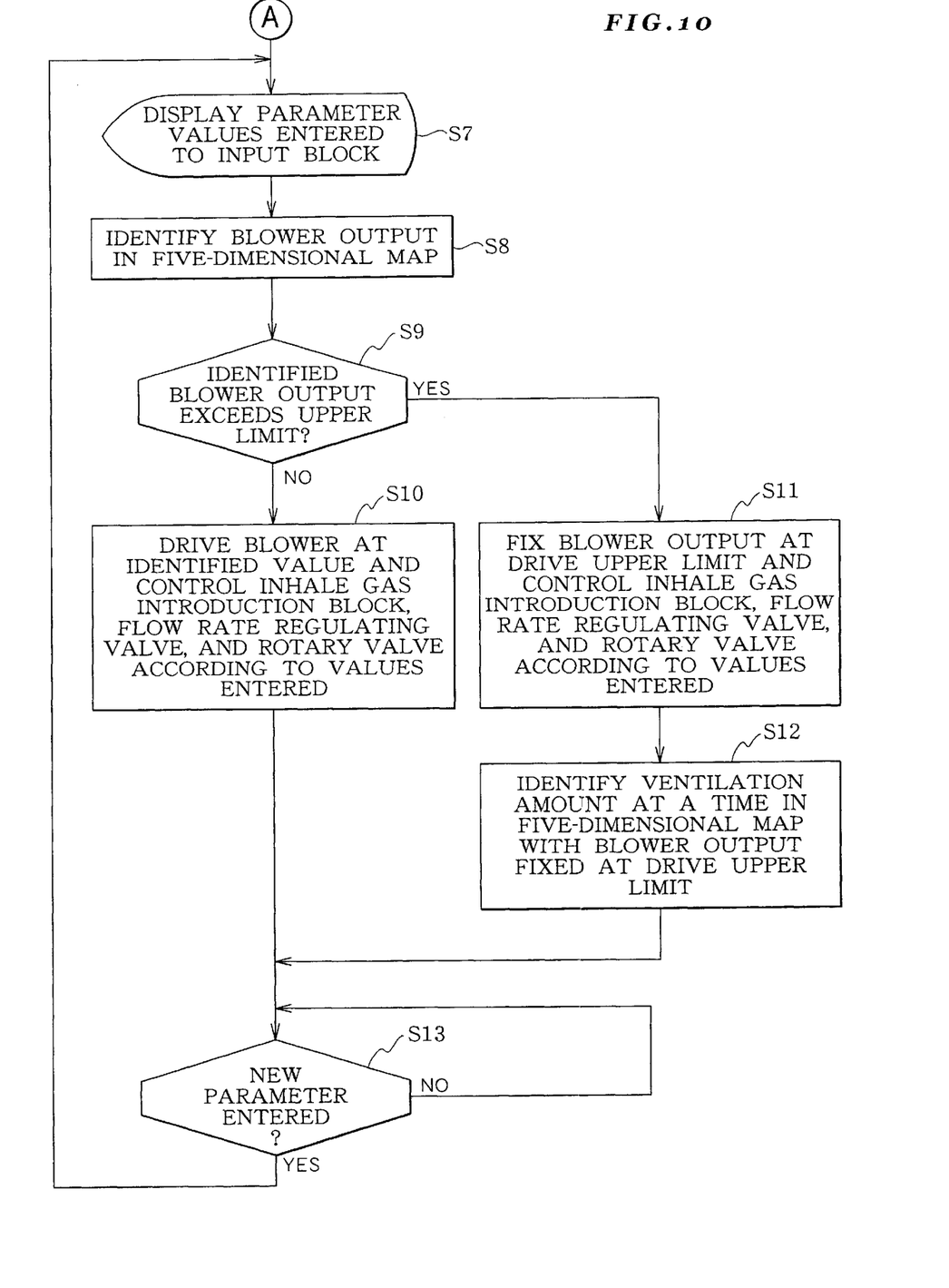
FIG. 10 is a continuation of the flowchart of FIG. 9.

Description will now be directed to the operation of the HFO artificial respiration apparatus 12 having the aforementioned configuration with reference to FIG. 1 to FIG. 10. FIG. 9 and FIG. 10 shows a flowchart showing the operation of the HFO artificial respiration apparatus 12.

Firstly, the input block 41 waits for an inner diameter of the in-trachea insert tube 81 to be entered (step S1). When an inner diameter value is entered through the operation panel 43, the input block 41 waits for an inhale gas supply amount (step S2). When an inhale gas supply amount value is entered through the operation panel 43, the input block 41 waits for an inhale gas oxygen concentration (step S3). When an inhale gas oxygen concentration value is entered through the operation panel 43, the input block 41 waits for a ventilation frequency to be entered (step S4). When a ventilation frequency value is entered through the operation panel 43, the input block 41 waits for an average inner pressure (step S5). When an average inner pressure value is entered through the operation panel 43, the input block 41 waits for a ventilation amount at a time for the patient X(step S6).

When a ventilation amount at a time for the patient X is entered and accepted by the input block 41, the operation control block 49 displays the aforementioned parameters on the display block 44 (step S7).

Next, in step 8, the blower output decider 45 references the five-dimensional map in the map memory 42 so as to identify an output of the blower 52 of the oscillating air pressure urging block 50 based on the inner diameter of the in-trachea insert tube 81, the inhale gas supply amount, the ventilation frequency, the average inner pressure, the ventilation amount at a time for the patient X which have been written into the input block 41.

Next, in step S9, a check is made to determine whether the identified output of the blower 52 exceeds the drive upper limit. Unless the identified blower output exceeds the drive upper limit, the blower output decider 45 causes to drive the blower 52 at the aforementioned identified output while the operation control block 49 performs an operation control of the inhale gas introduction block 62, the rotary valve 54, and the flow rate regulating valve 607 according to the parameters entered to the input block 41. Thus, the doctor as the operator can perform a HFO artificial respiration with a preferable ventilation amount at a time for the patient X (step S10).

Moreover, if the identified output of the blower 52 does exceed the drive upper limit, the blower 52 is driven at the drive upper limit while the operation control block 49 performs an operation control of the inhale gas introduction block 62, the rotary valve 54, and the flow rate regulating valve 607 according to the parameters entered to the input block 41.

Furthermore, the five-dimensional map is used to identify a ventilation amount at a time for the lungs of the patient X based on the inhale gas supply amount, the average inner pressure, the inner diameter of the in-trachea insert tube 81, and the ventilation frequency which have been entered to the input block 41 and the drive upper limit of the blower output, and the ventilation amount at a time thus obtained is displayed on the display block 44 (step S12, the drive upper limit maintaining function).

The HFO artificial respiration apparatus 12 performs a HFO artificial respiration according to the aforementioned control. When any of the parameters is updated during the HFO artificial respiration (step S13), the updated value is displayed on the display block 44 (step S) and the HFO artificial respiration is continued while performing the operation control of the inhale gas introduction block 62, the oscillating air pressure urging block 50, and the flow rate regulating valve 607 according to the updated parameter (step S8).

In the case when only the ventilation frequency is updated, the other parameters are maintained as they are and only the ventilation frequency is updated in referencing the five-dimensional map, so as to identify a new output of the blower 52 for use in an operation control. Here, since the ventilation amount at a time for the lungs of the patient has not been updated and the operation control is performed so as to maintain the ventilation amount at a time (ventilation amount maintaining function).

[Effects of the Invention]

In the aforementioned HFO artificial respiration apparatus 12, the operation control block 49 of the controller 40 has the ventilation amount maintaining function 46 and controls the amplitude of the blower 52 so as to maintain the ventilation amount at a time for the patient of the lungs at a constant value when the ventilation frequency is changed. This suppresses a sudden change of the ventilation amount at a time in a conventional example when the ventilation frequency is changed and enables to perform a stable HFO artificial respiration. Moreover, the operator (doctor) need not adjust the blower output by visual observation when changing the ventilation frequency.

Moreover, the present invention includes the map memory 42 containing the five-dimensional map having the ventilation amount at a time for the lungs of the patient X and the oscillating air pressure oscillation frequency as part of parameters and controls the output of the blower 52 by referencing the five-dimensional map. Accordingly, the doctor can perform a HFO artificial respiration while maintaining a desired ventilation amount at a time without measuring the actual ventilation amount at a time for the lungs of the patient.

Moreover, it is possible to maintain the ventilation amount at a time at a desired value with a high accuracy because the ventilation amount is decided by referencing the five-dimensional which based on a test data of actual measurements of the output of the blower 52.

Moreover, since the controller 40 includes the operation panel 43 for entering the parameters to the input block 41, there is no need to provide a separate input unit such as a personal computer for entering the parameters.

Furthermore, when a target output of the blower 52 exceeds the drive upper limit, the drive upper limit maintaining function 47 controls to fix the output of the blower 52 at the upper limit. Accordingly, it is possible to suppress a sudden change of the ventilation amount at a time for the lungs of the patient X, thereby suppressing a sudden change of the respiration state of the patient X.

Moreover, the ventilation amount at a time for the lungs of the patient X changed by this operation control is displayed on the display block 44. Accordingly, the doctor can recognize that the output of the blower 52 is insufficient and confirm the reduced ventilation amount at a time.

The present invention having the aforementioned configuration can provide a HFO artificial respiration apparatus having numerous advantages over the prior art.

The invention may be embodied in other specific forms without departing from the spirit or essential characteristic thereof. The present embodiments are therefore to be considered in all respects as illustrative and not restrictive, the scope of the invention being indicated by the appended claims rather than by the foregoing description and all changes which come within the meaning and range of equivalency of the claims are therefore intended to be embraced therein.

The entire disclosure of Japanese Patent Application No. 2000-2235 (Filed on Jan. 11, 2000) including specification, claims, drawings and summary are incorporated herein by reference in its entirety.

What is claimed is:

1. A high-frequency oscillation (HFO) artificial respiration apparatus comprising:
  an inhale gas introducer that supplies an inhale gas containing oxygen to a patient;
  a patient-side path for guiding the inhale gas from the inhale gas introducer to the patient,
  an oscillating air pressure urger that applies an oscillating air pressure having a shorter cycle than a respiration cycle of the patient, to the inhale gas flowing in the patient-side path,
  an exhaust path for exhausting into the atmosphere an exhale gas containing carbon dioxide exhaled from the patient; and
  a controller that controls the oscillating air pressure urger;
  wherein the oscillating air pressure urger includes an oscillation amplitude regulator that regulates an amplitude of the oscillating air pressure and a frequency regulator that regulates an oscillation frequency of the oscillating air pressure;
  wherein the controller includes an inputter that accepts setting inputs for specifying an oscillation frequency of the oscillating air pressure and a ventilation amount per unit time for the lungs of the patient and an operation controller that controls the frequency regulator and the amplitude regulator according to the inputs; and
  wherein the operation controller has a ventilation amount maintaining function for controlling an amplitude based on the amplitude regulator in such a manner that the ventilation amount per unit time for the lungs of the patient is maintained at a constant value when the oscillation frequency of the frequency regulator is changed by the setting inputs.

2. A HFO artificial respiration apparatus as claimed in claim 1, wherein the controller includes a map memory containing a map using the ventilation amount at a time for the lungs of the patient and the oscillation frequency of the oscillating air pressure as parameters for identifying an appropriate output of the amplitude regulator.

3. A HFO artificial respiration apparatus as claimed in claim 2, wherein the map is based on test data obtained by measuring the ventilation amount per unit time for the lungs of the patient while changing the output of the oscillating air pressure urger and the oscillation frequency of the oscillating air pressure.

4. A HFO artificial respiration apparatus as claimed in claim 3, the apparatus further comprising an input unit connected to the controller that enters the ventilation amount per unit time for the lungs of the patient and the oscillation frequency of the oscillating air pressure into the inputter.

5. A HFO artificial respiration apparatus as claimed in claim 4, the apparatus further comprising a display connected to the controller to display a predetermined information, wherein the operation controller has an output upper limit maintaining function, used when a target output of the oscillation regulator defined by the ventilation amount maintaining function exceeds a drive upper limit, for controlling the target output to be at the drive upper limit as well as displaying a corresponding ventilation amount per unit time for the lungs of the patient on the display.

6. A HFO artificial respiration apparatus as claimed in claim 3, the apparatus further comprising a display connected to the controller that displays a predetermined information, wherein the operation controller has an output upper limit maintaining function, used when a target output of the oscillation regulator defined by the ventilation amount maintaining function exceeds a drive upper limit, for controlling the target output to be at the drive upper limit as well as displaying a corresponding ventilation amount per unit time for the lungs of the patient on the display.

7. A HFO artificial respiration apparatus as claimed in claim 2, the apparatus further comprising an input unit connected to the controller that enters the ventilation amount per unit time for the lungs of the patient and the oscillation frequency of the oscillating air pressure into the inputter.

8. A HFO artificial respiration apparatus as claimed in claim 7, the apparatus further comprising a display connected to the controller to display a predetermined information, wherein the operation controller has an output upper limit maintaining function, used when a target output of the oscillation regulator defined by the ventilation amount maintaining function exceeds a drive upper limit, for controlling the target output to be at the drive upper limit as well as displaying a corresponding ventilation amount per unit time for the lungs of the patient on the display.

9. A HFO artificial respiration apparatus as claimed in claim 2, the apparatus further comprising a display connected to the controller that displays a predetermined information, wherein the operation controller has an output upper limit maintaining function, used when a target output of the oscillation regulator defined by the ventilation amount maintaining function exceeds a drive upper limit, for controlling the target output to be at the drive upper limit as well as displaying a corresponding ventilation amount per unit time for the lungs of the patient on the display.

10. A HFO artificial respiration apparatus as claimed in claim 1, the apparatus further comprising an input unit connected to the controller for entering the ventilation amount per unit time for the lungs of the patient and the oscillation frequency of the oscillating air pressure into the inputter.

11. A HFO artificial respiration apparatus as claimed in claim 10, the apparatus further comprising a display connected to the controller to display a predetermined information, wherein the operation controller has an output upper limit maintaining function, used when a target output of the oscillation regulator defined by the ventilation amount maintaining function exceeds a drive upper limit, for controlling the target output to be at the drive upper limit as well as displaying a corresponding ventilation amount per unit time for the lungs of the patient on the display.

12. A HFO artificial respiration apparatus as claimed in claim 1, the apparatus further comprising a display connected to the controller that displays a predetermined information, wherein the operation controller has an output upper limit maintaining function, used when a target output of the oscillation regulator defined by the ventilation amount maintaining function exceeds a drive upper limit, for controlling the target output to be at the drive upper limit as well as displaying a corresponding ventilation amount per unit time for the lungs of the patient on the display.

* * * * *